United States Patent [19]

Kain et al.

[11] Patent Number: 5,578,818
[45] Date of Patent: Nov. 26, 1996

[54] LED POINT SCANNING SYSTEM

[75] Inventors: Robert C. Kain, San Jose; Michael F. Miller, Mountain View; Lars Majlof, Saratoga, all of Calif.

[73] Assignee: Molecular Dynamics, Sunnyvale, Calif.

[21] Appl. No.: 438,416

[22] Filed: May 10, 1995

[51] Int. Cl.$^6$ .............................. H01J 3/14; G01N 21/64
[52] U.S. Cl. .................... 250/234; 250/458.1; 356/328
[58] Field of Search ................. 250/201.3, 234–235, 250/458.1, 459.1, 461.1, 461.2; 356/318, 326, 328

[56] References Cited

U.S. PATENT DOCUMENTS

| | | | |
|---|---|---|---|
| 4,827,125 | 5/1989 | Goldstein | 250/234 |
| 5,091,652 | 2/1992 | Mathies et al. | 250/458.1 |
| 5,125,746 | 6/1992 | Lipshitz | 250/201.3 |
| 5,151,580 | 9/1992 | Metlitsky et al. | 235/462 |
| 5,157,249 | 10/1992 | Hashimoto et al. | 250/201.5 |
| 5,190,857 | 3/1993 | Allen et al. | 250/459.1 |
| 5,192,980 | 3/1993 | Dixon et al. | 250/458.1 |
| 5,260,569 | 11/1993 | Kimura | 250/234 |
| 5,323,009 | 6/1994 | Harris | 250/458.1 |
| 5,377,004 | 12/1994 | Owen et al. | 250/458.1 |
| 5,381,224 | 1/1995 | Dixon et al. | 250/458.1 |
| 5,386,112 | 1/1995 | Dixon | 250/234 |

*Primary Examiner*—Stephone Allen
*Attorney, Agent, or Firm*—Thomas Schneck

[57] ABSTRACT

An LED point imaging scanner for stimulating and for reading fluorescent and reflective signal radiation from a target sample is disclosed. The LED light source is mounted on a scan head and is focused into the pinhole aperture of a spatial filter, then collimated and focused to a spot on the sample. The spatial filter in the illumination path, or an optical fiber serving the equivalent function, effectively restricts the incoherent LED light and creates a point light source. Signal radiation from the sample is collected through the scan head and the returning light beam is collimated and focused onto the receiving section of a detection means. A spatial filter in the path of the returning beam may also be utilized. The detection means is either a small detector which is mounted directly on the scan head or an end of an optical fiber which transmits the point image to a remotely-positioned stationary detector. The scan head is moved along one or two axes relative to the sample for scanning of a target area of the sample.

34 Claims, 6 Drawing Sheets

LED POINT SCANNING SYSTEM

TECHNICAL FIELD

This invention relates to moving head optical scanners for stimulating a target and for reading the fluorescent and reflective signal radiation that is returned from the target.

BACKGROUND ART

Moving head optical scanners for stimulation of target samples and for reading of the fluorescent and reflective signal radiation that emerges from the samples are used in many experimental formats. However, many existing scanners are limited with respect to scan speed, resolution, and field size because of their numerous components and the high mass of their optical assemblies. It is desirable to increase scan speed without compromising resolution in order to scan many samples in a short period of time.

The movement of a light beam to effect scanning in most optical scanners is generally accomplished via galvanometer scanning mechanisms or rotating polygonal mirrors. These devices are best suited for small fields when the same objective is utilized for both excitation and collection or large fields when a separate light collector is used, usually a nonimaging optic. When it is beneficial to have coaxial excitation and detection, scanning of large fields is best accomplished by moving the scan head or by moving the sample. The lens is used only for single point illumination and collection along the center of the optical axis.

Existing moving head systems use either a stationary light source, such as a xenon lamp or a gas laser, in conjunction with an optical fiber to deliver the excitation light to the scan head, or a compact laser diode, if the appropriate wavelength is available. Laser diodes are generally available at wavelengths of 635 nm and greater. Both alternatives can be complex and expensive.

A wide variety of scan formats is necessary for many research and diagnostic applications. In particular, the scanning of large gels using fluorescent labels is an emerging format.

It is therefore an object of the present invention to provide a versatile optical scanner of simple, lightweight, low-cost design for rapid scanning of a sample using a moving scan head design.

DISCLOSURE OF THE INVENTION

The above object has been achieved with an optical scanner having a Light Emitting Diode (LED) light source for point imaging of target samples. The LED provides a compact, inexpensive, and lightweight light source and thus can be housed directly within a movable scan head. The LED provides an illumination beam that is focused into a pinhole aperture of a spatial filter, then collimated and focused onto a spot on the sample. The pinhole defines the necessary resolution of the illumination beam and functions as an apparent point light source for forming the spot to be used to scan the sample. Alternatively, an optical fiber may be substituted for the spatial filter in the illumination beam path to restrict the beam to a point light source. Further, an optical fiber in the illumination beam path allows the LED to be removed from the scan head, if desired. The scan head is moved across the sample along one or two axes.

Fluorescence and reflective signal radiation returned from the illuminated spot on the sample may be gathered through the scan head and detected by a small detector placed directly on the scan head. A focusing lens and a spatial filter with a pinhole aperture may be provided in the return path leading to the detector, in order to enhance the detection of the returned signal radiation. Alternatively, an optical fiber may be used in the returning beam path to receive the fluorescence and reflection signals and to transmit them to the detector on the scan head or to a remote stationary detector. The returning light beam from the target sample is directed to the detection means via a wavelength discrimination filter, in the case of fluorescence detection, or by a partial reflection filter, for detection of reflection signals. The information regarding the returning light path is digitized and displayed or saved in a memory for future analysis.

The present invention has the advantage of allowing a light source for an optical scanner to be placed directly on the movable scan head. Since the light source is itself lightweight, compact, inexpensive, and powerful, it is well-suited to a rapid scanning system design. The point imaging of the present invention provides precise, location-specific information regarding the target sample. Additionally, it provides a collimated beam in the returning beam path which allows for the use of high performance interference filters for optimum illumination beam rejection.

BEST MODE OF CARRYING OUT THE INVENTION

Figure 1:
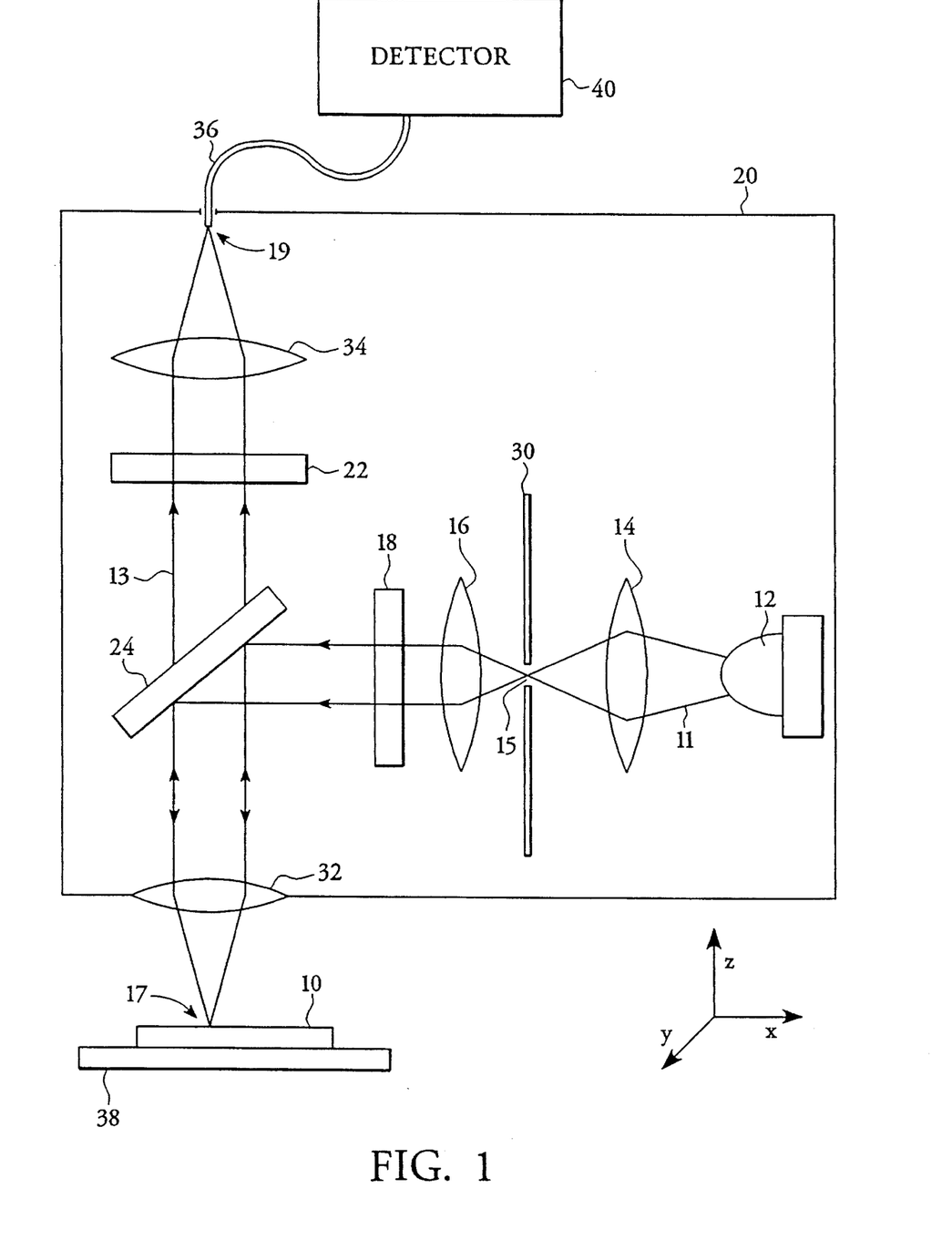
FIG. 1 is a plan view of a first embodiment of the LED point scanning system of the present invention.

With reference to FIG. 1, an LED light source 12 of scan head 20 provides an illumination beam 11 which is gathered by a first focusing lens 14 and then focused onto a spatial filter 30. The spatial filter 30 is provided with a pinhole 15. Illumination beam 11 is focused into pinhole 15 by first focusing lens 14 which is optimized to focus the illumination beam 11 with greatest possible energy density. Pinhole 15 is positioned at this point and effectively creates a point light source for the illumination optical path. After the illumination beam 11 passes through spatial filter 30, it is received and collimated by collimating lens 16. The collimated illumination beam then passes through a first filter 18 which defines the illumination wavelength band and then impinges upon beam splitter 24 which reflects at least a portion of the collimated illumination beam and directs it toward objective lens 32. Objective lens 32 then focuses the received portion of the collimated illumination beam onto sample 10 at a spot 17. Preferably, the numerical aperture of collimating lens 16 is equal to the numerical aperture of objective lens 32. This helps to provide the optimum energy density at the scan spot 17. Sample 10 is shown supported by a stage 38.

The incident beam 11 may cause reflective or fluorescent signal radiation to be returned from the illuminated spot 17 of sample 10. The signal radiation is collected by objective lens 32 and collimated into a returning light beam 13. At least a portion of returning light beam 13 passes through beam splitter 24 and then through second filter 22. After passing through second filter 22, the portion of the returning light beam 13 is then received by second focusing lens 34 and focused to a point 19 on the receiving section of a detection means.

The scan head 20 contains the LED 12 and the receiving section of the detection means. Scanning of the sample may be effected by moving the scan head 20 along a first axis to illuminate a plurality of spots along a scan line on the sample, e.g. the X-axis in FIG. 1, and then moving the stage 38, upon which the sample is supported, in a perpendicular axis. Alternatively, two-dimensional scan head movement may be desired and thus scanning may occur first along one axis and then along a second axis, perpendicular to the first axis, e.g. along the X- and Y-axes of FIG. 1. Thus, the Y-axis scan would cause illumination of spots on a plurality of parallel scan lines. The scan head 20 may be moved by a belt and pulley system, or other mechanical means.

As the scan head 20 moves, the LED point scanning system of the present invention causes sequential point-by-point illumination of the target area of the sample. Collection and detection of the illuminated spots causes a point-by-point imaging of that target area. The radiation collected from the sample is fluorescent, scattered, or reflected light from the illuminated spot on the sample. The signals received from each illuminated spot may be digitized, stored and mapped to a specific address corresponding to each spot. This mapping occurs in a computer memory or processor and is carried out for display purposes or for other analysis, such as data logging and statistical analysis. The proximity of the spots that are scanned in the point imaging system may be adjusted to correspond to the desired resolution of the analysis, e.g. contiguous or overlapping spots generally improve the clarity of the display.

FIG. 1 depicts a first embodiment of the optical system of the present invention. In the first embodiment, the returning light beam 13 is focused onto a spot 19, indicative of the point image of illuminated spot 17, by second focusing lens 34. The spot 19 is positioned at a first end of an optical fiber 36. The first end of optical fiber 36 is situated on the scan head 20. The second end of optical fiber 36 is connected to a stationary detector 40, which is positioned off the scan head 20. The point image of the illuminated spot on the sample is received by the optical fiber 36 and then is transmitted to the detector 40 for future analysis, e.g. by display of digitized data, as described above.

Figure 2:
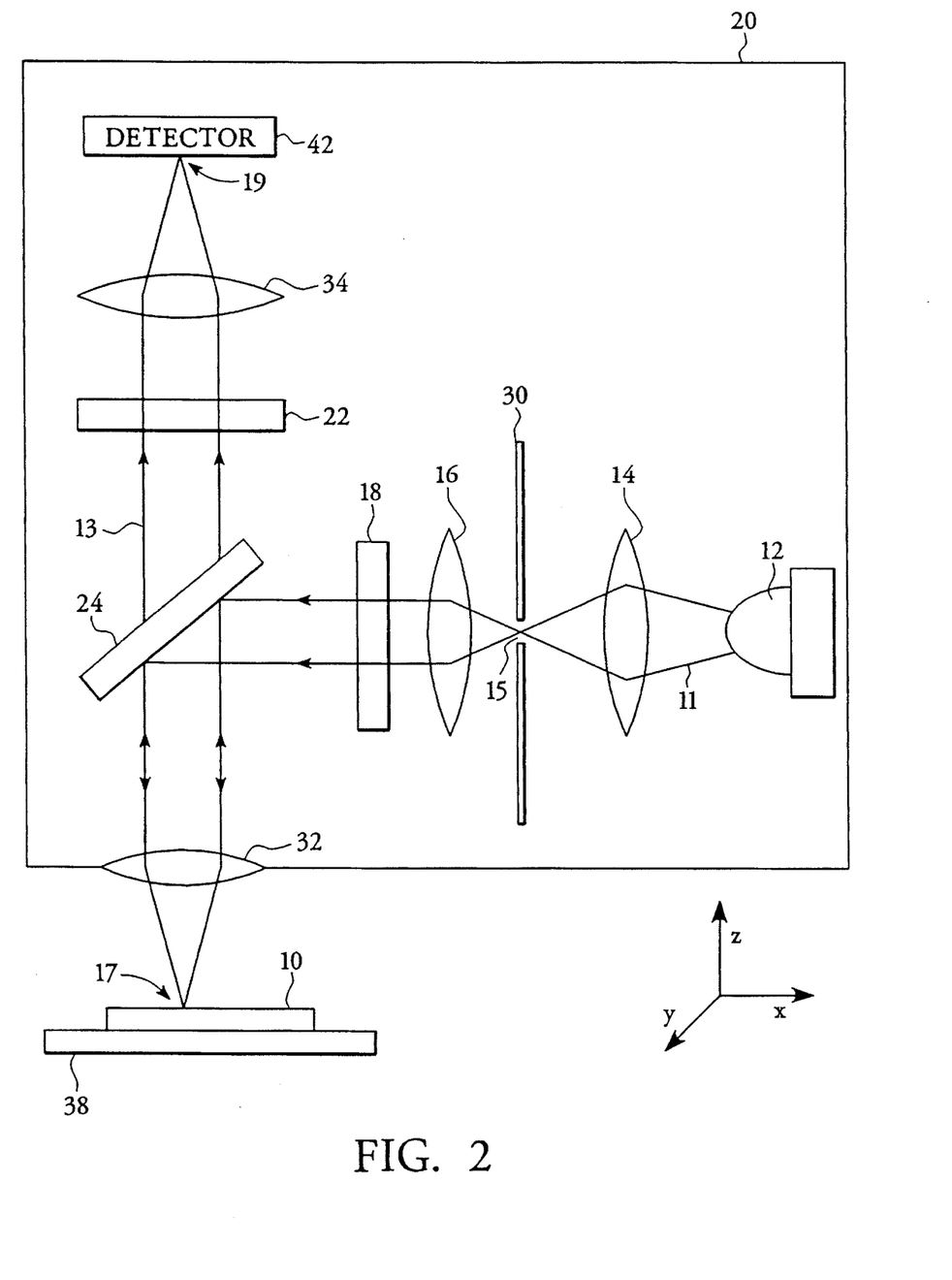
FIG. 2 is a plan view of a second embodiment of the LED point scanning system of the present invention.

In FIG. 2, illustrating a second embodiment of the present invention, the illumination beam path for the light incident upon the sample is the same as that shown in FIG. 1. The collection and detection along the returning beam path is also the same as in FIG. 1, with the exception that the returning light beam 13 is focused by second focusing lens 34 to a spot 19 which is directly received on the window of detector 42. Second focusing lens 34 may be omitted if the window of detector 42 is sufficiently large, however. Spot 19 is indicative of the point image of illuminated spot 17. Detector 42 is a small detector, such as a small photomultiplier tube or a solid state detector, and is lightweight and compact so that it may be placed directly on scan head 20, as seen in FIG. 2. As with the embodiment of FIG. 1, the scan head 20 may move along one or two axes.

Figure 3:
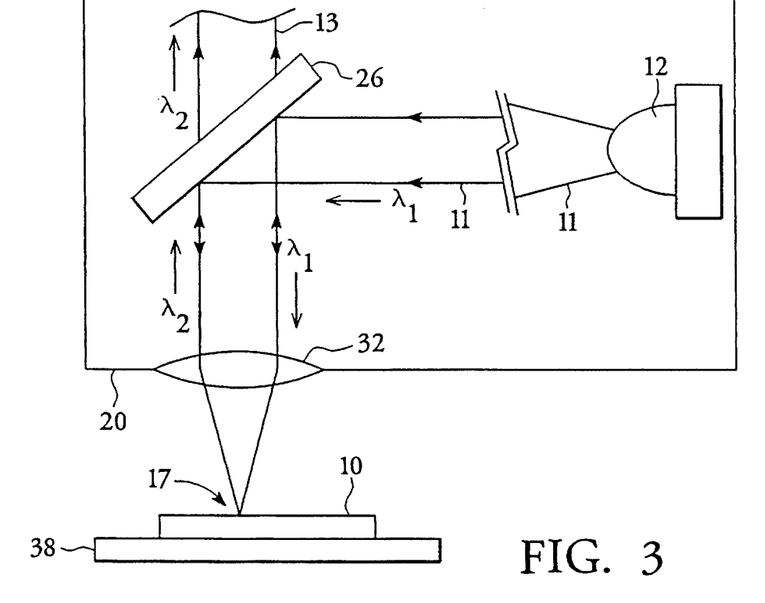
FIG. 3 depicts the use of a wavelength discrimination filter in the optical path of the present invention.
Figure 4:
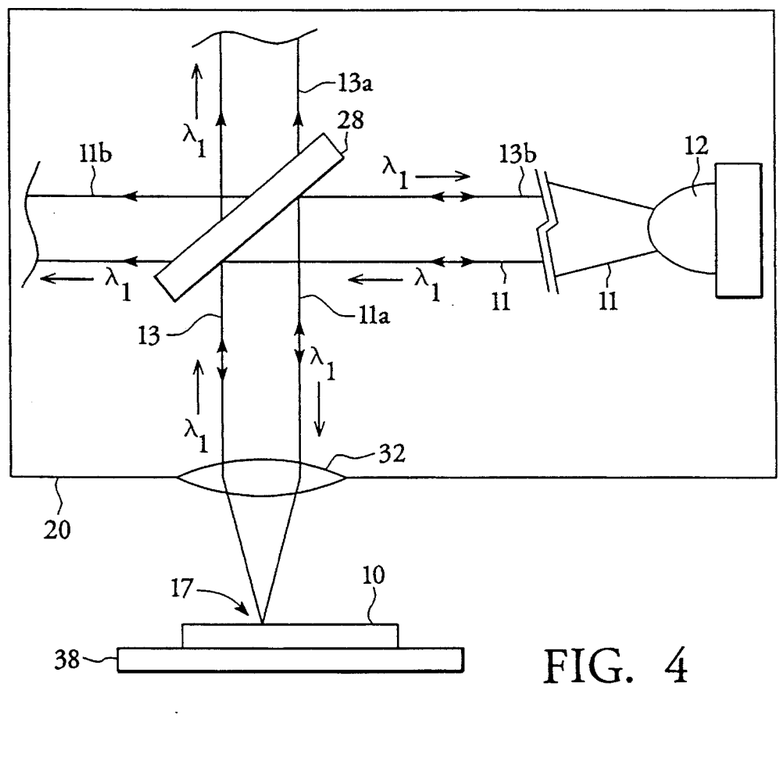
FIG. 4 depicts the use of a partial reflection filter in the optical path of the present invention.

FIGS. 3 and 4 depict different types of beam splitters, and are examples of beam splitter 24 of the first and second embodiments. In FIG. 3, a wavelength discrimination filter 26, such as a dichroic beam splitter, is placed in the path of the incident and returning light beams. Wavelength discrimination filter 26 is well-suited to fluorescence applications. Incoming illumination beam 11 of FIG. 3 is at an excitation wavelength $\lambda_1$. Illumination beam 11 is redirected by wavelength discrimination filter 26 and is made to impinge upon sample 10. Returning beam 13 is of a different wavelength, $\lambda_2$, than the wavelength of illumination beam 11, as is the case in fluorescence applications. Returning beam 13 is transmitted through wavelength discrimination filter 26 and then on toward the detector as in FIGS. 1 and 2. Thus, wavelength discrimination filter 26 is designed to reflect light of $\lambda_1$ and to transmit light of $\lambda_2$.

FIG. 4 shows the use of a different beam splitter than in FIG. 3. Partial reflection filter 28 is placed within the optical paths of the illumination and returning beams, 11 and 13 respectively. Partial reflection filter 28 is best-suited for applications requiring analysis of light reflected from samples. Illumination beam 11, having wavelength $\lambda_1$, impinges upon partial reflection filter 28, which typically has 50% reflection capabilities. A first portion 11a of illumination beam 11 is reflected by partial reflection filter 28 and redirected toward sample 10. A second portion 11b of illumination beam 11 is transmitted through partial reflection filter 28 and is unused in the optical system of the present invention. Reflective signal photons from sample 10, which form returning beam 13, have the same wavelength $\lambda_1$ as does illumination beam 11. Returning beam 13 impinges upon partial reflection filter 28 and a first portion 13a is transmitted through filter 28 and directed on toward a detector. A second portion 13b is reflected by partial reflection filter 28 and redirected back toward LED 12 along the path taken by the incoming illumination beam 11. This second portion 13b of returning beam 13 is unused for detection purposes in the optical system of the present invention.

It is best to substitute the particular beam splitter needed in the place of general beam splitter 24 shown in the FIG. 1 and FIG. 2 embodiments. For example, either wavelength discrimination filter 26 or partial reflection filter 28 may be used depending upon the desired application. Because the returning beam 13 is of the same wavelength as the illumination beam 11 in reflection scanning, a wavelength discrimination filter is not the preferred method of splitting the optical paths for reflection applications. Similarly, when the illumination beam 11 and the returning beam 13 are of different wavelengths, as in fluorescence scanning, a partial reflection filter is not the preferred method of directing the beam as the use of such a filter results in unused portions of the beams.

Figure 5:
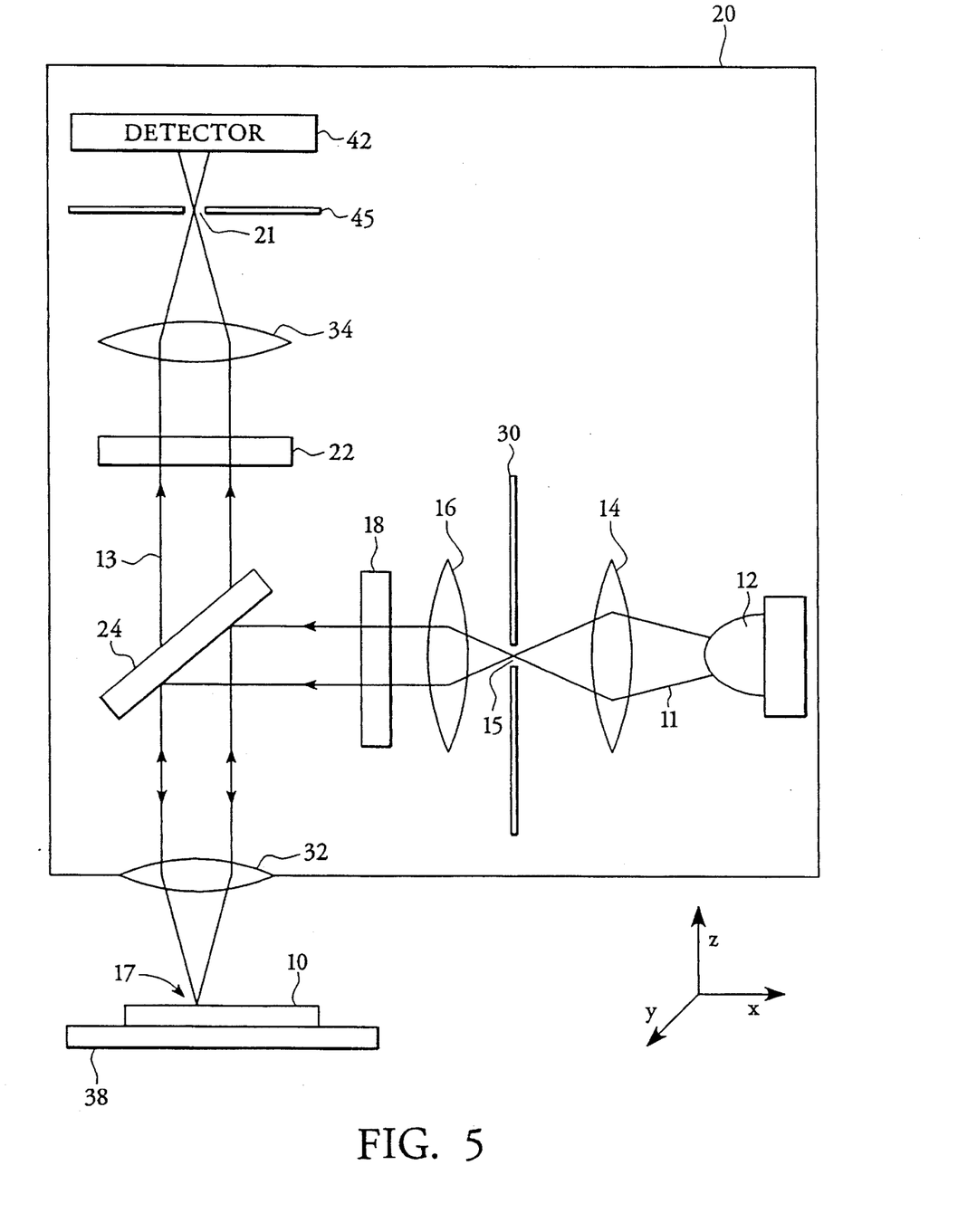
FIG. 5 depicts a variation of the embodiment of FIG. 2, having a spatial filter in the returning light beam path.

As stated above, focusing lens 34 need not be in the returning light beam path, but rather its use is dependent upon the type of detection means utilized. Another element that may be helpful in the return path is a second spatial filter 45 having pinhole aperture 21, as seen in FIG. 5. The returning light beam 13 is focused by focusing lens 34 into pinhole aperture 21, thus limiting the amount of scattered light collected. In this case, the restriction of returning beam 13 within pinhole 21 is equivalent to spot 19 of FIG. 2. Detector 42 may then be positioned behind the detection spatial filter 45 in a spaced-apart format, as shown, or it may adjoin spatial filter 45. The addition of spatial filter 45 to the returning light beam path effectively creates a classic confocal system which may be desired for some applications. For some purposes, removal of illumination spatial filter 30 from the optical configuration illustrated in FIG. 5 may be useful. Also, an optical fiber may be used in place of spatial filter 45 to restrict the returning light beam in a manner analogous to fiber 44 of FIG. 6, discussed below, and to transmit the returning light beam toward the detector.

Figure 6:
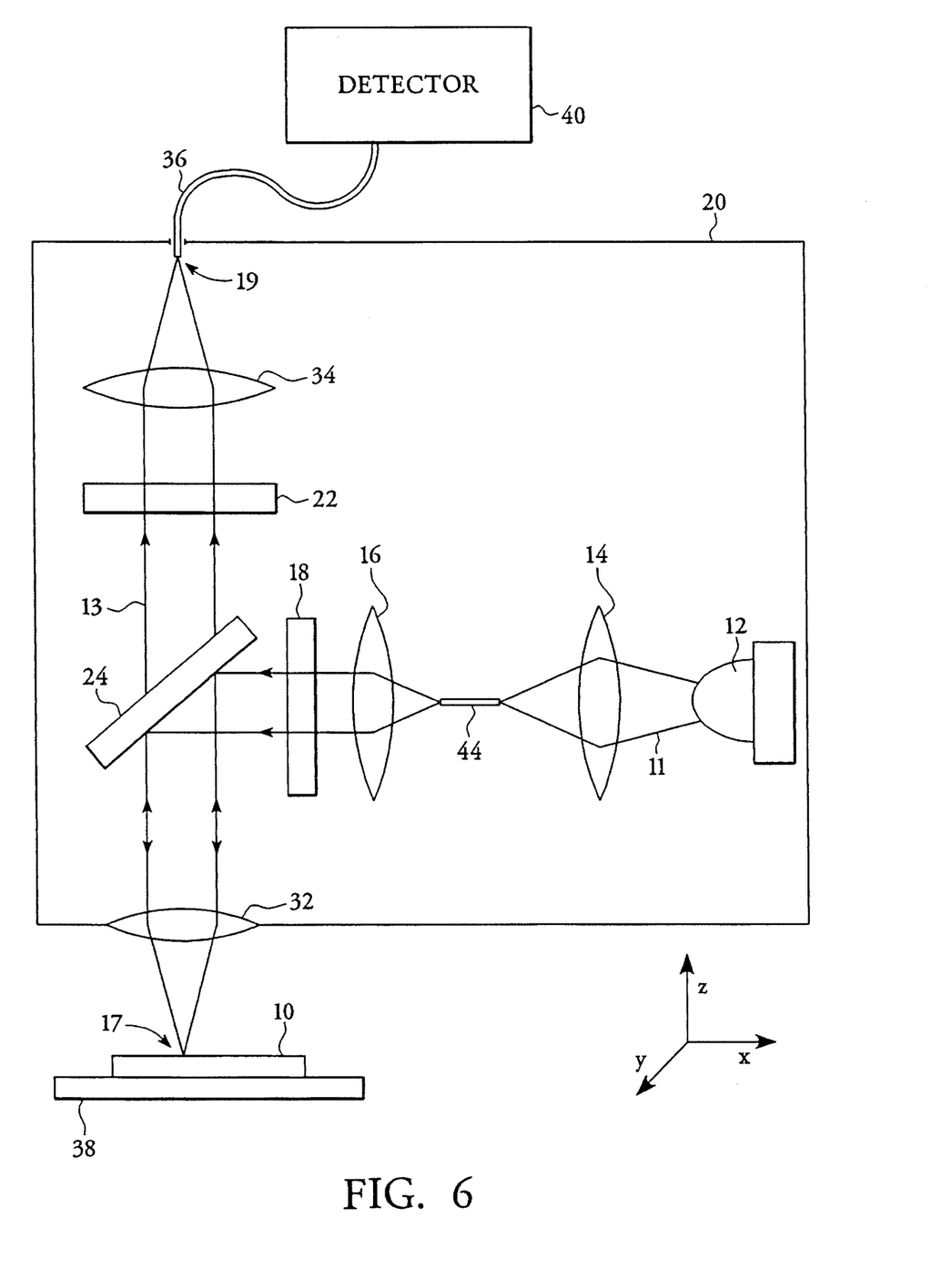
FIG. 6 depicts a third embodiment of the LED point scanning system of the present invention.
Figure 7:
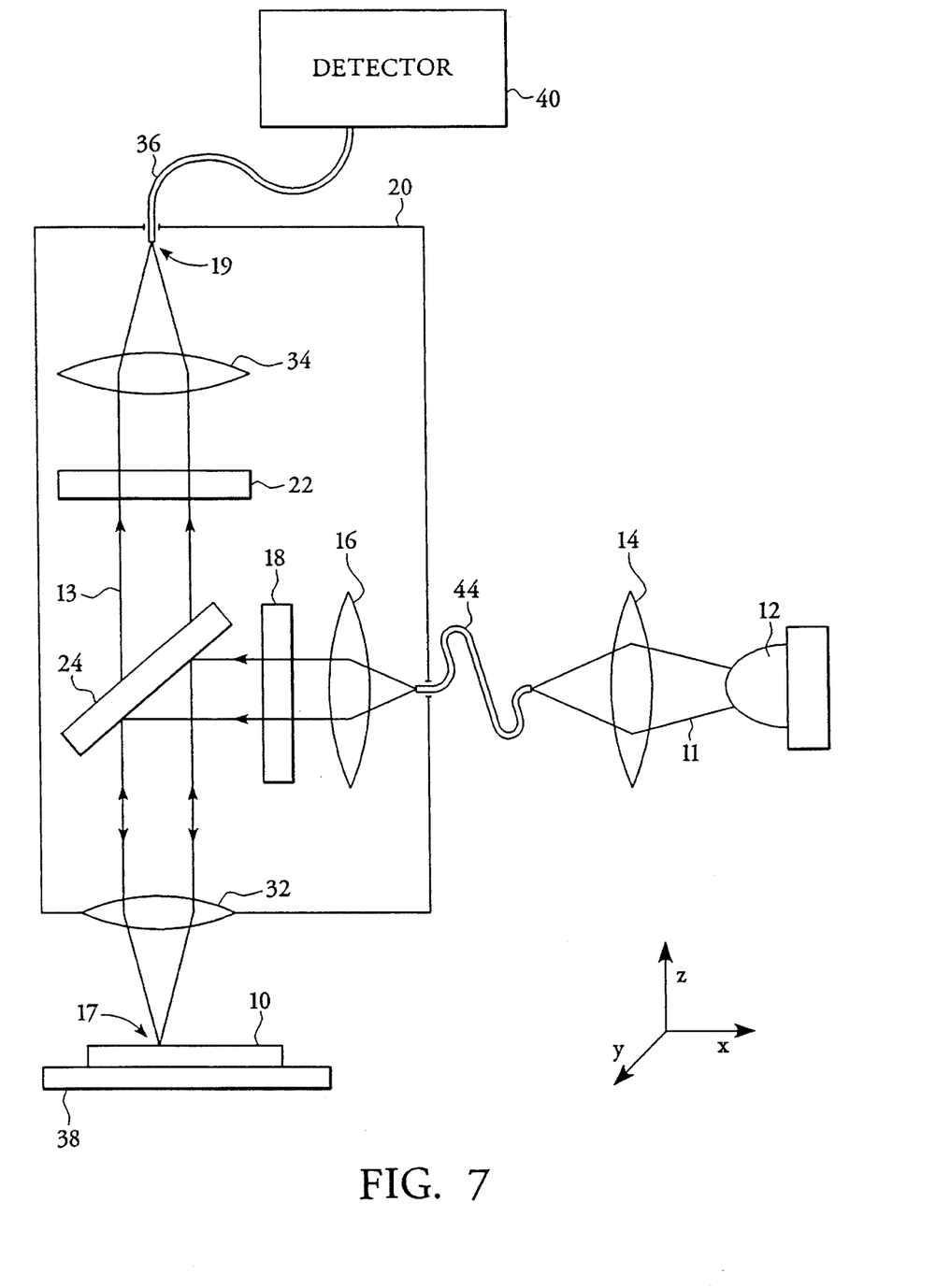
FIG. 7 depicts a variation of the embodiment of FIG. 6, wherein the LED light source is removed from the scan head.

FIG. 6 illustrates an alternate embodiment of the present invention. The excitation spatial filter 30, which serves to narrow the illumination beam 11 to a point source, has been replaced by an optical fiber 44. The placement of first focusing lens 14 and collimating lens 16 has also been altered, so that the focal points of these two lenses do not coincide, as in FIG. 1, but instead are spaced apart, with fiber 44 between them. The focal point of lens 14 coincides with an entrance end of fiber 44 and the focal point of lens 16 coincides with an exit end of fiber 44. Thus, the illumination beam 11 passes through lens 14, is focused into fiber 44 and transmitted through fiber 44, and is then received and collimated by lens 16. Optical fiber 44 effectively acts as a spatial filter in the illumination path because it restricts the beam and creates a point source, which is advantageous in the LED point scanning system of the present invention. Although this embodiment has been illustrated in FIG. 6 as a variation of the embodiment in FIG. 1, with respect to the returning beam path, it may also be described as a variation of the FIG. 2 or FIG. 5 embodiments. For example, optical fiber 44 may be utilized in the illumination path where the specifics of the returning light beam detection optics do not include an optical fiber, as in fiber 36, leading to a remote stationary detector, as in detector 40, but rather include a small detector mounted on the scan head.

Where there is an optical fiber in the illumination beam path as in FIG. 6, the LED 12 and lens 14 need not be mounted on scan head 20. Optical fiber 44 then serves to transmit the illumination beam to the optics within the scan head. FIG. 7 illustrates this variation, wherein LED 12 and lens 14 are in a remote stationary location, and optical fiber 44 receives and transmits the illumination beam from this source to the optics of movable scan head 20. As before, the specifics of the returning light beam optics may vary from those shown in FIG. 7.

The collimation of segments of both the illumination beam 11 and the returning beam 13 is effected in order to best use the beam splitter and the filters in the optical paths, which work best at given angles of incidence.

Spatial filter 30 having pinhole 15 is used in the present invention because LED 12, an incoherent light source, serves as the illumination source of the point scanning system. The focal spot size of an incoherent light source is limited by the filament or chip size of the LED. The pinhole is typically smaller than the limited spot size and therefore provides higher scan resolution. A laser diode light source, which would not require a limiting pinhole, is another small and lightweight light source. However, laser diodes are more expensive than LEDs, and are generally limited to very few wavelengths.

The LED point scanning system of the present invention may be used in a wide variety of situations, such as fluorescent imaging of electrophoretic gels, blots, and membranes, tissue sections and other biological samples, reading of storage phosphor screens, and reflective imaging. Depending upon the desired application, the scan head may be outfitted with the most effective type of beam splitter and the appropriate detection means. In all embodiments, the present invention provides an inexpensive, versatile point scanner for rapid imaging of samples.

We claim:

1. An LED optical system for point scanning of a sample comprising:

(a) a movable scan head having
   (i) an LED light source providing an illumination beam along a single path,
   (ii) an illumination spatial filter having a pinhole aperture spaced apart from the light source,
   (iii) means for focusing the illumination beam into the pinhole aperture,
   (iv) means for directing the illumination beam after the illumination beam has been focused into the pinhole aperture onto a spot of the sample to cause signal radiation to be returned from the sample, and
   (v) means for collecting and detecting the signal radiation returned from the sample,
(b) a stage for supporting the sample, and
(c) means for moving the scan head along a first axis relative to the stage to illuminate a plurality of spots along a scan line on the sample.

2. The system of claim 1 further comprising:

means for moving the scan head along a second axis relative to the stage to cause illumination of spots on a plurality of parallel scan lines on the sample, the second axis being perpendicular to the first axis.

3. The system of claim 1 wherein the means for directing the illumination beam onto a spot of the sample comprises:

a collimating lens for receiving and collimating the illumination beam after the illumination beam has been focused into the pinhole aperture, and an objective lens for focusing the collimated illumination beam onto a spot of the sample.

4. The system of claim 3 wherein the collimating lens has a numerical aperture and the objective lens has a numerical aperture, the numerical apertures of the collimating lens and the objective lens being equal.

5. The system of claim 1 wherein the means for collecting and detecting the signal radiation returned from the sample comprises:

an objective lens for directing the signal radiation to form a collimated returning light beam, and a focusing lens for receiving at least a portion of the collimated returning light beam and focusing the portion into an optical fiber, the fiber transmitting the returning light beam to a stationary detector removed from the movable scan head.

6. The system of claim 5 further comprising a beam splitter disposed in the path of the returning light beam, wherein the beam splitter comprises a wavelength discrimination filter.

7. The system of claim 5 further comprising a beam splitter disposed in the path of the returning light beam, wherein the beam splitter comprises a partial reflection filter.

8. The system of claim 1 wherein the means for collecting and detecting the signal radiation returned from the sample comprises:

an objective lens for directing the signal radiation to form a collimated returning light beam, and a detector for receiving at least a portion of the returning light beam, the detector being mounted on the movable scan head.

9. The system of claim 8 further comprising:

a focusing lens, disposed between the objective lens and the detector, for receiving at least a portion of the collimated returning light beam and focusing the portion onto the detector.

10. The system of claim 8 further comprising:

a detection spatial filter having a pinhole aperture, disposed between the objective lens and the detector, and a focusing lens, disposed between the objective lens and the detection spatial filter, for receiving at least a portion of the collimated returning light beam and focusing the portion into the pinhole aperture of the detection spatial filter.

11. The system of claim 8 further comprising a focusing lens, disposed between the objective lens and the detector, for receiving at least a portion of the collimated returning light beam and focusing the portion into an optical fiber, the fiber transmitting the returning light beam toward the detector.

12. The system of claim 8 further comprising a beam splitter disposed in the path of the returning light beam, wherein the beam splitter comprises a wavelength discrimination filter.

13. The system of claim 8 further comprising a beam splitter disposed in the path of the returning light beam, wherein the beam splitter comprises a partial reflection filter.

14. An LED optical system for point scanning of a sample comprising:
   (a) an LED light source providing an illumination beam along a single path,
   (b) means for focusing the illumination beam into an optical fiber, the fiber transmitting the illumination beam,
   (c) a movable scan head having
      (i) means for receiving the transmitted illumination beam from the fiber and for directing the illumination beam onto a spot of the sample to cause signal radiation to be returned from the sample, and
      (ii) means for collecting and detecting the signal radiation returned from the sample,
   (d) a stage for supporting the sample, and
   (e) means for moving the scan head along a first axis relative to the stage to illuminate a plurality of spots along a scan line on the sample.

15. The system of claim 14 further comprising:
   means for moving the scan head along a second axis relative to the stage to cause illumination of spots on a plurality of parallel scan lines on the sample, the second axis being perpendicular to the first axis.

16. The system of claim 14 wherein the LED light source and the means for focusing the illumination beam into an optical fiber are mounted on the movable scan head.

17. The system of claim 14 wherein the means for collecting and detecting the signal radiation returned from the sample comprises:
   an objective lens for directing the signal radiation to form a collimated returning light beam, and
   a focusing lens for receiving at least a portion of the collimated returning light beam and focusing the portion into an optical fiber, the fiber transmitting the returning light beam to a stationary detector removed from the movable scan head.

18. The system of claim 14 wherein the means for collecting and detecting the signal radiation returned from the sample comprises:
   an objective lens for directing the signal radiation to form a collimated returning light beam, and
   a detector for receiving at least a portion of the returning light beam, the detector being mounted on the movable scan head.

19. A moving scan head for point imaging of a sample, the scan head comprising:
   an LED source providing an illumination beam along a single path,
   an illumination spatial filter having a pinhole aperture,
   a first focusing lens disposed between the LED source and the illumination spatial filter for focusing the illumination beam into the pinhole aperture of the illumination spatial filter,
   a collimating lens for collimating the illumination beam after the illumination beam has been focused into the pinhole aperture,
   a beam splitter disposed in the illumination beam path for reflecting at least a portion of the collimated illumination beam,
   an objective lens for receiving the portion of the illumination beam from the beam splitter and for focusing the portion of the illumination beam onto a spot of the sample to cause signal radiation to emerge from the sample, and for receiving and collimating the signal radiation from the sample to form a collimated returning beam, the beam splitter also disposed in the returning beam path for passing at least a portion of the collimated returning beam, and
   a receiving section of a detection means disposed to intercept the returning beam.

20. The scan head of claim 19 further comprising:
   a second focusing lens for receiving the portion of the collimated returning beam that has passed through the beam splitter and for focusing the portion of the collimated returning beam onto the receiving section of the detection means.

21. The scan head of claim 19 further comprising:
   a detection spatial filter having a pinhole aperture disposed in the path of the returning beam, and
   a second focusing lens for receiving the portion of the collimated returning beam that has passed through the beam splitter and for focusing the portion of the collimated returning beam into the pinhole aperture of the detection spatial filter.

22. The scan head of claim 19 wherein the collimating lens has a numerical aperture and the objective lens has a numerical aperture, the numerical apertures of the collimating lens and the objective lens being equal.

23. The scan head of claim 19 wherein the beam splitter disposed in the illumination beam path for reflecting at least a portion of the collimated illumination beam and disposed in the returning beam path for passing at least a portion of the collimating returning beam comprises a wavelength discrimination filter.

24. The scan head of claim 19 wherein the beam splitter disposed in the illumination beam path for reflecting at least a portion of the collimated illumination beam and disposed in the returning beam path for passing at least a portion of the collimating returning beam comprises a partial reflection filter.

25. The scan head of claim 19 wherein the detection means is a photomultiplier tube mounted on the scan head.

26. The scan head of claim 19 wherein the detection means is a solid state detector mounted on the scan head.

27. The scan head of claim 19 wherein the receiving section of the detection means is an end of an optical fiber, the fiber transmitting the returning beam to the detection means.

28. An LED point scanner for imaging of a sample, the scanner comprising:
   (a) an incident beam means having
      (i) a movable light source providing an illumination beam from an LED along a single path,
      (ii) a spatial filter having a pinhole aperture, (iii) means for focusing the illumination beam into the pinhole aperture, (iv) means for collimating the illumination beam after the illumination beam has been focused into the pinhole aperture, and (v) means for receiving the collimated illumination beam and for focusing the collimated illumination beam onto a spot of the sample to cause signal radiation to be returned from the sample, (b) an outgoing beam means having (i) means for collecting and collimating the signal radiation from the sample into a returning beam, and (ii) means for focusing the collimated returning beam onto a receiving section of a detection means, and (c) means for moving the incident and outgoing beam means to provide for scanning along a first axis relative to the sample.

29. The scanner of claim 28 further comprising:

means for moving the incident and outgoing beam means to provide for scanning along a second axis relative to the sample, the second axis being perpendicular to the first axis.

30. The scanner of claim 28 wherein the receiving section of the detection means is a window of a photomultiplier tube, the photomultiplier tube being mounted on the scan head.

31. The scanner of claim 28 wherein the receiving section of the detection means is a window of a solid state detector, the solid state detector being mounted on the scan head.

32. The scanner of claim 28 wherein the receiving section of the detection means is an end of an optical fiber, the fiber transmitting the returning beam to a stationary detector.

33. The scanner of claim 28 further comprising a beam splitter included in the incident and outgoing beam means, wherein the beam splitter comprises a wavelength discrimination filter.

34. The scanner of claim 28 further comprising a beam splitter included in the incident and outgoing beam means, wherein the beam splitter comprises a partial reflection filter.

* * * * *